United States Patent [19]
Henry et al.

[11] Patent Number: 4,769,322
[45] Date of Patent: Sep. 6, 1988

[54] QUANTIFICATION OF ENDOGENOUS HISTAMINE

[75] Inventors: David P. Henry; Kenneth M. Verburg, both of Indianapolis, Ind.

[73] Assignee: Eli Lilly and Company, Indianapolis, Ind.

[21] Appl. No.: 929,564

[22] Filed: Nov. 12, 1986

Related U.S. Application Data

[63] Continuation of Ser. No. 599,850, Apr. 12, 1984, abandoned.

[51] Int. Cl.[4] .......................... C12Q 1/48; C12N 9/10
[52] U.S. Cl. ..................................... 435/15; 435/193; 435/815
[58] Field of Search ........... 435/15, 191, 193, 814–816

[56] References Cited

PUBLICATIONS

Axelrod, J., "Histamine-N-Methyltransferase (Pig Liver)", Methods in Enzymology, vol. XVII B: 766–769 (1971).
Sellinger et al., J. Neurochemistry, 30: 437–445 (1978).
Verberg et al., Federation Proceedings 41, 1709 (1982).
Verburg et al. "A New . . . N–Methyltransferase" Life Sciences 32, 2855–2867 (1983).
Bowsher et al. "Rat Histamine . . . Properties" The Journal of Biological Chemistry 258, No. 20, 12215–12220 (1983).
Bowsher et al. Abstract of Oral Presentation given at Apr. 13, 1983 FASEB Meeting.
Correa et al. "Increase . . . rats" Brain Research 205, 445–451 (1981).
Brown et al. "Enzymatic N–Methylation of Histamine" Nature 183, 680 (1959).
Salberg et al. "A Reverse . . . Methods" Life Sciences 21, No. 10, 1439–1446 (1977).
Miller et al. "Application of . . . Plasma" The Journal of Pharmacology and Experimental Therapeutics 175, 228–234 (1970).
Taylor et al. "Histamine . . . Decarboxylase" The Journal of Pharmacology and Experimental Therapeutics 179, 619–633 (1971).
Taylor et al. "Isotopic . . . Tissue" Journal of Neurochemistry 19, 1343–1358 (1972).
Snyder et al. "A Sensitive . . . Histamine" The Journal of Pharmacology and Experimental Therapeutics 153, 544–549 (1966).
Shaff et al. "Increased . . . Serum" Analytical Biochemistry 94, 425–430 (1979).
Moss et al. "Role of . . . Humans" Anesthesiology 55, 19–25 (1981).
Beaven et al. "Modification . . . Urine" Clinica Chimica Acta 37, 91–103 (1972).
Horakova et al. "Blood . . . Assay" Clinica Chimica Acta 79, 447–456 (1977).
Guilloux et al. "Enzymatic . . . Histamine" Clinica Chimica Acta 116, 269–275 (1981).
Lorenz et al. "A Sensitive . . . Plasma" Hoppe-Seyler's Z. Physiol. Chem. 353, 911–920 (1972).
Brown et al. "A Sensitive . . . Individuals" Analytical Biochemistry 109, 142–146 (1980).
Kobayashi et al. "A Single-Isotope . . . Histamine" Analytical Biochemistry 46, 85–90 (1972).
Blumenthal et al. "Isotope . . . Release" Biochemical Medicine 11, 312–317 (1974).

Primary Examiner—Esther M. Kepplinger
Attorney, Agent, or Firm—Bruce J. Barclay; Leroy Whitaker

[57] ABSTRACT

A new procedure for isolating histamine N-methyltransferase in pure form has permitted the development of a new and highly sensitive radioenzymatic assay for histamine.

5 Claims, No Drawings

QUANTIFICATION OF ENDOGENOUS HISTAMINE

This application is a continuation of application Ser. No. 599,850, filed Apr. 12, 1984, now abandoned.

BACKGROUND OF THE INVENTION

Histamine is an important biogenic amine which functions in diverse physiologic roles in mammals. For example, histamine plays a role in allergic hypersensitivity reactions, modulation of gastric acid secretion, and is believed to function as a neurotransmitter in the central nervous system. For a detailed discussion of histamine and its functions within the human body, see chapter 26 of Goodman and Gilman's *The Pharmacological Basis of Therapeutics*, 6th Edition 1980.

Due to the importance of histamine in biologic systems, accurate and reliable methods for determining the level of histamine in the body are critical to provide proper diagnosis. Further, since histamine is present in the body in very small amounts, the methods must be highly sensitive, that is, capable of detecting the compound in very small amounts. The frequency at which these methods are conducted mandate further that they be highly reproducible under laboratory conditions when employing a variety of body tissues and fluids and provide the results quickly in order to facilitate patient recovery.

Radioenzymatic assays are sensitive analytical methods which have found wide use in the quantification of various biogenic amines, including histamine. These methods are based on the enzyme catalyzed methylation of a substrate of interest to a radiolabeled product using radiolabeled S-adenosylmethionine as the methyl donor. The radiolabeled reaction product is then selectively isolated and quantified by scintillation spectrometry.

The histamine N-methyltransferase catalyzed methylation of histamine to tritiated N-τ-methylhistamine has been widely used as the basis for development of a histamine radioenzymatic assay. However, due to the use of relatively impure enzyme preparations, current procedures lack the necessary sensitivity and specificity to quantify histamine in important biologic samples, such as human plasma and urine.

Accordingly, the present invention describes an improved radioenzymatic assay for histamine employing highly purified histamine N-methyltransferase. The use of purified histamine N-methyltransferase in the present histamine radioenzymatic assay dramatically improves assay sensitivity and specificity by removing competing methyltransferases and small molecules. Therefore, the use of purified histamine N-methyltransferase permits the development of a substantially improved assay system for the quantification of histamine in biologic samples.

SUMMARY OF THE INVENTION

The present invention relates to a method for quantifying histamine in mammalian body tissue comprising the following steps:

A. combining an appropriate amount of a mammalian body tissue sample with substantially purified histamine N-methyltransferase, tritiated S-adenosylmethionine, a potassium phosphate buffer and water to provide a solution;

B. incubating the solution prepared in (A) under agitation at a temperature in the range of about 0° C. to about 5° C. until substantially all of the histamine has been methylated to tritiated N-τ-methylhistamine;

C. adding a 2.0 to 2.5M potassium borate buffer with a pH in the range of about 9.5 to about 12 to the solution in (B);

D. extracting the tritiated N-τ-methylhistamine from the solution in (C) with an organic solvent system in which the tritiated N-τ-methylhistamine is preferentially soluble;

E. transferring the supernatant following centrifugation of the mixture in (D) to a separate container containing a potassium phosphate buffer with a pH in the range of about 6.5 to about 7.5;

F. isolating the aqueous phase from the solution in (E);

G. combining the aqueous phase in (F) with from about 1% to about 5% by weight of bis-diethylhexylhydrogen phosphate, a potassium phosphate buffer at a pH in the range of about 7.0 to about 7.5, and a scintillation cocktail; and H. counting the radiation emitted from the tritiated N-τ-methylhistamine.

DETAILED DESCRIPTION OF THE INVENTION

In the present histamine radioenzymatic assay, the presence of histamine in a mammalian tissue sample is chemically determined by the methylation of histamine with tritiated S-adenosylmethionine in the presence of histamine N-methyltransferase to afford tritiated N-τ-methylhistamine and counting the radiation emitted therefrom. This procedure is represented by the following scheme:

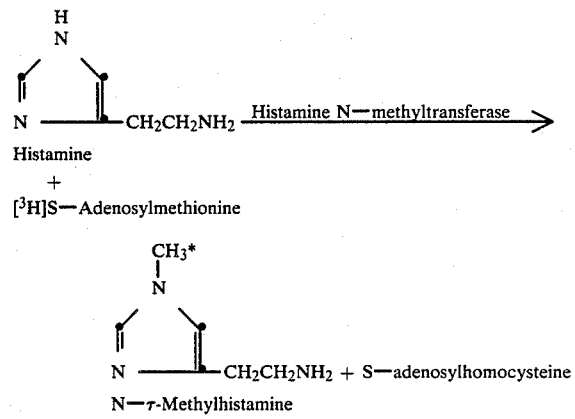

It is known that histamine is present throughout the body. Therefore, due to the high degree of sensitivity of the present assay, a variety of different mammalian body tissues may be employed in the present assay in order to quantify the presence of this biogenic amine. Exemplary histamine containing body tissues that are easily obtainable include blood plasma, nasal secretions, tears, earwax, hair and the like.

It is known that basophils are a rich source of endogenous histamine. Therefore, care should be exercised when collecting blood samples for analysis in the present assay in order to minimize cell lysis. Typically the blood is collected using EDTA as an anticoagulent. The mixture is then centrifuged and the plasma is isolated therefrom.

The term "substantially purified histamine N-methyltransferase", as used herein, is defined as an enzyme having a homogenous composition essentially free from foreign contaminants. It has been determined experimentally that the purity of the enzyme used in the present radioenzymatic assay is critical in affording adequate sensitivity and specificity in the present histamine assay. Competing methyltransferases which are likely contaminants of impure enzyme preparations are believed to reduce the sensitiviy of the assay by exhausting the tritiated S-adenosylmethionine. Further, these contaminants produce S-adenosylhomocysteine, a potent inhibitor of most methyltransferases. The use of purified histamine N-τ-methyltransferase in the present histamine assay has allowed the inclusion of low concentrations of highly specific active tritiated S-adenosylmethionine and the development of a simplified solvent extraction product isolation procedure. The following procedure illustrates the method for obtaining substantially purified histamine N-methyltransferase suitable for use in the present histamine assay.

Histamine N-methyltransferase is widely distributed in a number of mammalian tissue types. Guinea pig brain has been used extensively as a source of the enzyme, but rat kidney is preferably employed as the enzyme source since this tissue is easily obtainable, relatively stable and contains a high concentration of the enzyme. The enzyme containing tissue is removed from the appropriate source and, if necessary, all of the fatty tissue is removed from around the tissue. The isolated tissue is immediately chilled to about 0° C., for instance by submersion in an ice cold saline solution.

The tissue must be disrupted in order to facilitate extraction of the enzyme. Tissue disruption may be conducted mechanically by any of several well known procedures such as sonication, by means of a tissue press, or preferably by homogenization. Disruption of the tissue is conducted in the presence of an isotonic media in order to extract the histamine N-methyltransferase contained therein. While a variety of suitable isotonic solutions do exist, such as potassium chloride, dilute phosphate buffer or water, a sucrose solution is preferably employed. The preparation is centrifuged and the supernatant is then centrifuged for a period of 30 to 90 minutes in the range of about 150,000 to about 250,000 xg. Preferably the supernatant is centrifuged at 220,000 xg for about 1 hour.

The pH of the supernatant is adjusted to approximately 4.5 to 5.5 by the slow addition of an appropriate weak acid, which is any acid capable of forming a buffer in this pH range. The preferred weak acid employed herein is cold acetic acid. The resulting suspension is centrifuged and the supernatant is titrated to a pH of approximately 6.5 to 7.5 by the addition of a cold base such as ammonium hydroxide. A sufficient volume of one or more chelating agents such as EDTA, preferably at pH of approximately 7, may be added to provide stability to the histamine N-methyltransferase.

Next, the enzyme preparation is fractionated by the addition of sufficient solid ammonium sulfate to the enzyme preparation to provide a concentration of ammonium sulfate between about 2.0 and about 3.2M (50–85% saturation). The final precipitate is collected by centrifugation and suspended in a buffer having a pH in the range of about 7.0 to about 8.0. Acceptable buffers for use in the method include the tris buffers, such as tris(hydroxymethyl)aminomethane, and especially phosphate buffers, such as potassium phosphate. These buffers may also contain one or more reducing agents such as mercaptoethanol, dithioerythritol and especially dithiothreitol. The quantity of buffer, and reducing agent if present, employed herein is not critical. The resulting solution is then dialyzed for a period of 12 to 24 hours with an acceptable buffer as defined above. One or more buffer changes may be necessary during the dialysis step.

The buffers employed in the method of purification can be selected from among those acceptable buffers defined above. However, it should be noted that the buffer used in each step of the method must be chemically compatible with the buffer used in the prior step(s). Therefore it is preferred to use the same buffer in each of the steps in the present method.

The following two chromatographic procedures may be conducted under either an aerobic or anaerobic surrounding. When conducted under anaerobic conditions, an inert gas such as helium, nitrogen or argon is typically passed through the column. While a reducing agent as defined above may be employed under either procedure, such an agent must be used when using aerobic chromatographic conditions.

The dialyzed enzyme prepared above is next purified with anion exchange chromatography employing for example, a diethylaminoethyl or triethylaminoethyl anion exchange column typically equilibrated with a buffer at a pH in the range of about 6.5 to about 8.5. The buffer employed in this step may be chosen from those acceptable buffers defined above, and must be compatible with the buffer used previously. The type of chromatographic material employed in this step consists of a diethylaminoethyl moiety, for example, covalently attached to any of a variety of matrices such as cellulose or any other polymer. A variety of these chromatographic materials are commercially available and the preferred material is sold by Pharmacia Fine Chemicals as Sephacel. Fractions containing the enzyme are identified by standard procedures. For example, a protein elution profile is determined by any one of a variety of procedures such as UV spectrometry at 280 nanometers. However, histamine N-methyltransferase activity is localized by assays known in the art designed to indicate the enzyme's presence. Fractions containing maximum enzyme activity are combined and concentrated by well known procedures such as ultrafiltration employing a membrane capable of retaining substances of a molecular weight greater than approximately 25,000.

Due to the potential instability of histamine N-methyltransferase the concentrated protein from the chromatographic procedure described above is immediately chromatographed on a molecular size exclusion chromatography column which has been previously equilibrated with a compatible buffer having a pH in the range of about 6.5 to about 8.5. Fractions containing histamine N-methyltransferase are combined and concentrated typically by ultrafiltration. This procedure is taught and claimed in U.S. patent application Ser. No. 599,849, filed Apr. 12, 1984.

Dilutions conducted for the present assay are conducted in culture tubes other than glass, for example polystyrene, since histamine is absorbed by glass. Incubations are preferably conducted in appropriate size borosilicate culture tubes in order to facilitate volumetric transfers. All measurements are preferably conducted in duplicate. For comparison, reference standards are also generally prepared with and without histamine.

The assay tubes are preferably prepared as follows. While the exact quantity of material in the assay tubes may vary depending on the quantity of material available, preferably the smallest possible quantity of reagents are employed due to cost considerations. Preferably, a culture cube is charged with 25 μl of sample and 10 μl of water.

The reaction is initiated by the addition of a solution containing tritiated S-adenosylmethionine and the purified enzyme histamine N-methyltransferase. Preferably, this solution is prepared immediately prior to use due to the potential inactivation of the reagents. Also contained in the solution is a potassium phosphate buffer at a pH in the range of about 7.5 to 8.0. For example, in a 20 tube assay, 250 μl of 0.5M potassium phosphate at pH 7.8, 50 μl of tritiated S-adenosylmethionine (75-85 Ci/mmol) and 200 μl of histamine N-methyltransferase are combined and 25 μl of the resulting solution is added to each of the assay tubes prepared above.

Tritiated S-adenosylmethionine is the labeled methyl donor employed in the present enzymatic methylation of histamine. This tritium labeled methyl donor can be made by art known radiochemical methods and is commercially available from New England Nuclear Corporation and Amersham-Searle. The tritium label is at the methyl position. It has now been found that this methyl donor should be present in the incubation mixture at a concentration ≧ about 1 μM for maximal activity. In order to produce the excellent sensitivity of this assay, the labeled methyl donor is essentially free of unlabeled, cold methyl donor S-adenosylmethionines. The addition of unlabeled cold methyl donor makes the assay less sensitive for the quantification of histamine. If a less sensitive assay is desired, this may be achieved by adding unlabeled, cold S-adenosylmethionine to the assay incubate. The tritium labeled S-adenosylmethionine should be prepared with maximum radioactivity for maximum sensitivity of the assay. Radioactivity should be greater than or equal to about 8 Ci/mmol. Preferred radioactivity is from about 75 to about 85 Ci/mmol.

The tubes are next vortexed and incubated at a temperature in the range of about 0° to about 5° C. The reaction is conducted until substantially all of the histamine has been methylated to tritiated N-τ-methylhistamine. Generally the reaction will be complete after about 30 to 90 minutes, more preferably after about 60 minutes. Conducting the incubation at this temperature increases the specificity of the reaction for histamine. It has been determined that methylation of other potential substrates for histamine N-methyltransferase is reduced at this temperature while the methylation of histamine is maintained. Furthermore, this temperature affect is a unique characteristic of this enzyme in this assay since other methyltransferases, such as phenylethanolamine N-methyltransferase and catechol-O-methyltransferase, are inhibited at approximately 0° C.

The reaction is terminated upon the addition of a 2.0 to 2.5M potassium borate buffer with a pH in the range of about 9.5 to about 12, more preferably with a pH of approximately 11.

Next a solvent mixture in which the tritiated N-τ-methylhistamine is preferentially soluble is added to the preparation. Preferably, a solvent mixture of toluene and isopentyl alcohol, ideally in a ratio of 3:1 by volume, is added to the tubes. Each of the tubes are then stoppered and gently vortexed. The contents of the tubes are then separated by centrifugation.

The supernatant is next isolated and transferred to a second tube containing a potassium phosphate solution at a pH in the range of 6.5 to 7.5. These second tubes are stoppered, vortexed and centrifuged, and the organic layer is removed by aspiration. Another quantity of the solvent mixture is preferably added to each of the culture tubes which are again vortexed and centrifuged. The organic phase is removed by aspiration.

The aqueous phase thus isolated is transferred to a scintillation vial that contains from about 1% to about 5% by weight of bis-diethylhexylhydrogen phosphate (DEHP), a potassium phosphate buffer with a pH in the range of 7.0 to 7.5, and a scintillation cocktail. The preferred amount of DEHP is 2% by weight. A wide variety of scintillation cocktails are known and used such as Econofluor, a cocktail commercially available from New England Nuclear Corporation. The vials are then shaken and the contents are quantified by liquid scintillation spectrometry according to well known procedures by counting the radiation emitted from the tritiated N-τ-methylhistamine.

The following procedure illustrates the histamine assay of the present invention.

Histamine Assay

Dilutions of histamine standards were carried out in polystyrene culture tubes. Incubations, however, were done in 12 mm×75 mm disposable borosilicate culture tubes to facilitate volumetric transfers. All samples were assayed in duplicate. The 50 μl total incubation volume was formed by the sequential addition of 25 μl of a biological sample, either 10 μl of water or 10 μl of water containing 0.5 ng of histamine (internal standard).

The enzyme reaction was then initiated by the addition of 25 μl of a reaction reagent. The reaction reagent for a 20 tube assay was made immediately prior to use and consisted of 250 μl of a 0.5M potassium phosphate solution at a pH of 7.8, 50 μl of tritiated S-adenosylmethionine (75-85 Ci/mm) and 200 μl of histamine N-methyltransferase. In summary, every 25 μl of sample was incubated with and without a 10 μl internal standard, 10 μl of histamine N-methyltransferase, 2.5 μl of tritiated S-adenosylmethionine in a 0.1 M potassium phosphate solution at pH 7.8. Blanks and external standards consisted of 25 μl of reaction reagent, 25 μl of water or dilute buffer replacing the sample and 10 μl of water with or without 0.5 ng of histamine, respectively. Following the addition of the reaction reagent, the tubes were gently vortexed and incubated in a water bath for 60 minutes at 0°-5° C.

The reaction was terminated by the addition of 75 μl of a 2.5M potassium borate solution with a pH of 11. Four milliliters of toluene-isopentyl alcohol (3:1) were added and the tubes were stoppered and vortexed. The tubes were then centrifuged briefly at room temperature to facilitate phase separation.

Next, 3.8 ml of the organic phase was transferred to a second tube containing 250 μl of a 1.0M potassium phosphate solution at a pH of 7.1. The tubes were stoppered, vortexed and centrifuged. The organic layer was then removed by aspiration. Another 1.25 ml of toluene-isopentyl alcohol (3:1) was added and the tubes were vortexed and centrifuged. The organic layer was removed by aspiration and 150 μl of the aqueous phase was transferred to a scintillation vial that contained 2 percent bis-diethylhexylhydrogen phosphate in Econofluor. The vials were shaken by hand and quantified by liquid scintillation spectrometry. The amount of histamine present in the sample was calculated by the following formula:

Histamine (pg) =

$$\frac{\text{sample (cpm)} - \text{blank (cpm)}}{\text{internal standard (cpm)} - \text{sample (cpm)}} \times 500 \text{ pg}$$

We claim:

1. A method for quantifying histamine in mammalian body tissue comprising the following steps:
   A. combining an appropriate amount of a mammalian body tissue sample with substantially purified histamine N-methyltransferase, tritiated S-adenosylmethionine, a potassium phosphate buffer and water to provide a solution;
   B. incubating the solution prepared in (A) under agitation at a temperature in the range of about 0° C. to about 5° C. until substantially all of the histamine has been methylated to tritiated N-τ-methylhistamine;
   C. adding a 2.0 to 2.5 M potassium borate buffer with a pH in the range of about 9.5 to about 12 to the solution in (B);
   D. extracting the tritiated N-τ-methylhistamine from the solution in (C) with an organic solvent system in which the tritiated N-τ-methylhistamine is soluble;
   E. transferring the supernatant following centrifugation of the mixture in (D) to a separate container containing a potassium phosphate buffer with a pH in the range about 6.5 to about 7.5;
   F. isolating the aqueous phase from the solution in (E);
   G. combining the aqueous phase in (F) with from about 1% to about 5% by weight of bis-diethylhexylhydrogen phosphate, a potassium phosphate buffer at a pH in the range of about 7.0 to about 7.5, and a scintillation cocktail; and
   H. counting the radiation emitted from the tritiated N-τ-methylhistamine;

wherein the method for obtaining substantially purified histamine N-methyltransferase comprises the following steps:
   A. disrupting a suitable mammalian tissue in the presence of an isotonic media and isolating the soluble histamine N-methyltransferase by centrifugation;
   B. adjusting the pH of the supernatant in (A) to about 4.5 to about 5.5 with an appropriate weak acid;
   C. fractionating the solution in (B) with ammonium sulfate at a concentration of about 50% to about 85% and collecting the precipitate;
   D. purifying the enzyme preparation in (C) with anion exchange chromatography; and
   E. purifying the enzyme preparation in (D) with molecular size exclusion chromatography in the presence of an inert gas.

2. A method of claim 1 wherein the mammalian body tissue analyzed is blood plasma.

3. A method of claim 1 wherein the potassium borate buffer has a pH of about 11.

4. A method of claim 1 wherein the organic solvent system in which the tritiated N-τ-methylhistamine is soluble is toluene:isopentyl alcohol in a ratio of 3:1 by volume.

5. A method of claim 1 wherein the bisdiethylhexylhydrogen phosphate is present at a concentration of 2% by weight.

* * * * *